US009885703B2

(12) United States Patent
Ninomiya et al.

(10) Patent No.: US 9,885,703 B2
(45) Date of Patent: Feb. 6, 2018

(54) EVALUATION METHOD AND SCREENING METHOD FOR SPHINGOSINE-1-PHOSPHATE 1 (S1P1) RECEPTOR AGONISTS

(71) Applicant: MEIJI SEIKA PHARMA CO., LTD., Tokyo (JP)

(72) Inventors: Tomohisa Ninomiya, Yokohama (JP); Satoshi Yoshida, Yokohama (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/912,827

(22) PCT Filed: Aug. 20, 2014

(86) PCT No.: PCT/JP2014/071737
§ 371 (c)(1),
(2) Date: Feb. 18, 2016

(87) PCT Pub. No.: WO2015/025871
PCT Pub. Date: Feb. 26, 2015

(65) Prior Publication Data
US 2016/0195513 A1 Jul. 7, 2016

(30) Foreign Application Priority Data
Aug. 20, 2013 (JP) ................................ 2013-170383

(51) Int. Cl.
*G01N 33/50* (2006.01)
*C07K 14/705* (2006.01)
*G01N 33/15* (2006.01)
*A61K 49/00* (2006.01)

(52) U.S. Cl.
CPC ....... *G01N 33/502* (2013.01); *A61K 49/0008* (2013.01); *G01N 33/5008* (2013.01); *C07K 14/705* (2013.01); *G01N 33/15* (2013.01); *G01N 2500/10* (2013.01)

(58) Field of Classification Search
CPC ............. G01N 33/502; G01N 33/5008; G01N 2500/10; G01N 33/15; A61K 49/0008; C07K 14/705
See application file for complete search history.

(56) References Cited

U.S. PATENT DOCUMENTS

| 2010/0113528 A1 | 5/2010 | Ahmed et al. |
| 2013/0217663 A1 | 8/2013 | Yoshida et al. |

FOREIGN PATENT DOCUMENTS

| JP | 2010-524886 A | 7/2010 |
| WO | 2013/094761 A1 | 6/2013 |

OTHER PUBLICATIONS

Andrew J. Brown, et al., "Functional coupling of mammalian receptors to the yeast mating pathway using novel yeast/mammalian G protein α-subunit chimeras", Yeast, Jan. 15, 2000, pp. 11-22, vol. 16, No. 1.
Klemens Budde, et al., "First Human Trial of FTY720, a Novel Immunomodulator, in Stable Renal Transplant Patients", Journal of the American Society of Nephrology, 2002, pp. 1073-1083, vol. 13, No. 4.
Kenji Chiba, "A New Therapeutic Approach for Autoimmune Diseases by the Sphingosine 1-Phosphate Receptor Modulator, Fingolimod "FTY720), The Pharmaceutical Society of Japan, 2009, pp. 655-665, vol. 129, No. 6.
Peter Gergely, et al., "The selective sphingosine 1-phosphate receptor modulator BAF312 redirects lymphocyte distribution and has species-specific effects on heart rate", British Journal of Pharmacology, Nov. 2012, pp. 1035-1047, vol. 167, No. 5.
Jennifer J. Hill, et al., "Inhibition of a $G_i$-activated Potassium Channel (GIRK1/4) by the $G_q$-coupled m1 Muscarinic Acetylcholine Receptor", The Journal of Biological Chemistry, Affinity Sites, Feb. 23, 2001, pp. 5505-5510, vol. 276, No. 8.
Jennifer J. Hill, et al., "Inhibition of a $G_i$-activated Potassium Channel (GIRK1/4) by the $G_q$-coupled m1 Muscarinic Acetylcholine Receptor", The Journal of Biological Chemistry, Feb. 23, 2001, pp. 5505-5510, vol. 276, No. 8.
Herbert M. Himmel, et al., "Evidence for Edg-3 Receptor-Mediated Activation of $I_{KACh}$ by Sphingosine-1-Phosphate in Human Atrial Cardiomyocytes", Molecular Pharmacology, 2000, pp. 449-454, vol. 58.
Suzanne Mandala, et al., "Alteration of Lymphocyte Trafficking by Sphingosine-1-Phosphate Receptor Agonists", Science, 2002, pp. 346-349, vol. 296.
Trung H.M. Pham, et al., "S1P$_1$ Receptor Signaling Overrides Retention Mediated by Gα$_i$-Coupled Receptors to Promote T Cell Egress", Immunity, Jan. 2008, pp. 122-133, vol. 28, No. 1.
M. Germana Sanna, et al., "Sphingosine 1-Phosphate (S1P) Receptor Subtypes S1P$_1$, and S1P$_3$, Respectively, Regulate Lymphocyte Recirculation and Heart Rate", The Journal of Biological Chemistry, Apr. 2, 2004, pp. 13839-13848, vol. 279, No. 14.
Aude Saulière, et al., "Deciphering biased-agonism complexity reveals a new active AT$_1$, receptor entity", Nature Chemical Biology, Jul. 2012, pp. 622-630, vol. 8.
Satoshi Yoshida, "Novel S1P1 receptor agonists with unique intracellular signaling", 246th national meeting of the American-Chemical-Society (ACS ), Sep. 8, 2013. pp. 65, vol. 246.
Satoshi Yoshida, et al., "Gai2/Gai3 Biased-S1P1 Receptor Agonist no Sosei: Juyotai Karyu Signal Sentaku ni yoru Shindokusei Keigen", The 31st Medicinal Chemistry Symposium, Abstracts, Nov. 1, 2013, pp. 168, vol. 31.

(Continued)

*Primary Examiner* — Robert Landsman
(74) *Attorney, Agent, or Firm* — Sughrue Mion, PLLC

(57) ABSTRACT

It has been found that a main effect (immunosuppressive activity) of an S1P1 receptor agonist correlates with the selectivity for cells expressing a combination of an S1P1 receptor with Gαi2 or Gαi3, and that an adverse effect (cardiotoxicity) of an S1P1 receptor agonist correlates with the selectivity for cells expressing a combination of an S1P1 receptor with Gαi1.

10 Claims, No Drawings

(56) References Cited

OTHER PUBLICATIONS

Liang Zhi, et al., "FTY720 Blocks Egress of T Cells in Part by Abrogation of Their Adhesion on the Lymph Node Sinus", The Journal of Immunology, Sep. 1, 2011, pp. 2244-2251, vol. 187, No. 5.
International Search Report of PCT/JP2014/071737, dated Nov. 25, 2014. [PCT/ISA/210].
Written Opinion of PCT/JP2014/071737, dated Nov. 25, 2014. [PCT/ISA/237].
International Preliminary Report on Patentability dated Mar. 3, 2016, issued by the International Bureau in corresponding application No. PCT/JP2014/071737.
M. Forrest et al.; "Immune Cell Regulation and Cardiovascular Effects of Sphingosine 1-Phosphate Receptor Agonists in Rodents Are Mediated via Distinct Receptor Subtypes"; The Journal of Pharmacology And Experimental Therapeutics, vol. 309, No. 2, Feb. 6, 2004, pp. 758-768.
Communication, dated Dec. 13, 2016, issued by the European Patent Office in corresponding European Patent Application No. 14838211.2.

EVALUATION METHOD AND SCREENING METHOD FOR SPHINGOSINE-1-PHOSPHATE 1 (S1P1) RECEPTOR AGONISTS

CROSS REFERENCE TO RELATED APPLICATIONS

This application is a National Stage of International Application No. PCT/JP2014/071737 filed Aug. 20, 2014, claiming priority based on Japanese Patent Application No. 2013-170383, filed Aug. 20, 2013, the contents of all of which are incorporated herein by reference in their entirety.

TECHNICAL FIELD

The present invention relates to a method for evaluating an immunosuppressive activity and cardiotoxicity of a sphingosine-1-phosphate 1 (hereinafter referred to as "S1P1") receptor agonist, and a screening method for an S1P1 receptor agonist having a potent immunosuppressive activity and a low cardiotoxicity.

BACKGROUND ART

Symptoms of many autoimmune disease are developed as a result of an abnormal immune response which proliferates and activates lymphocytic cells to erroneously recognize the own organism, and attack a certain tissue or the entire body of the own organism. The cause varies and has not been revealed yet. Heretofore, aiming at a drug for suppressing the proliferation and activation of lymphocytic cells, various immunosuppressants have been developed and clinically applied. However, such immunosuppressants have non-negligible adverse effects due to non-specific, cell-proliferation suppressing activity and cytotoxic action, bringing about problems.

Recently, Fingolimod (as known as FTY-720) having been approved as a drug against relapsing-remitting multiple sclerosis has attracted attention as a drug with a novel mechanism because it regulates immunity by controlling localization of lymphocytic cells without depleting the lymphocytic cells through the cell death. However, on the other hand, Fingolimod has a problem that serious adverse effects have been observed mainly on the cardiovascular system, including bradycardia and cardiac arrhythmia such as an atrioventricular block (AV block) (NPLs 1, 2).

A sphingosine-1-phosphate (hereinafter referred to as "S1P") receptor is a G protein-coupled receptor (GPCR) present on the cell membrane, and five subtypes of the receptor have been identified (S1P1, S1P2, S1P3, S1P4, and S1P5; as known as endothelial differentiation genes EDG-1, EDG-5, EDG-3, EDG-6, and EDG-8). It is known that Fingolimod phosphorylated in vivo (FTY-p) binds to S1P1, S1P3, S1P4, and S1P5 receptors, and acts as an agonist.

Lymphocytic cells constantly circulate in circulating blood and lymphoid tissues at certain intervals. It is known that an S1P1 receptor on the lymphoid cell membrane has quite an important role when the lymphocytic cells migrate from a lymphoid tissue into circulating blood. An S1P1 receptor agonist represented by FTY-p binds mainly to an S1P1 receptor on lymphocytic cells and incorporates the S1P1 receptor into the cells, so that the S1P1 receptor on the lymphocytic cells disappears. Thereby, the lymphocytic cells are then sequestered in secondary lymphoid tissues, reducing the number of circulating lymphocytes. As a result, the S1P1 receptor agonist exhibits an excellent immunosuppressive activity (NPL 2). Meanwhile, it is believed from the studies on rodents that stimulating an S1P3 receptor expresses adverse effects on the cardiovascular system such as bradycardia (NPLs 3, 4). Hence, the studies on an S1P1 receptor agonist having a lowered action on an S1P3 receptor have been in progress.

In such circumstances, recently, a clinical test outcome has been reported regarding BAF312 (as known as Siponimod), an agonist selective for S1P1 and S1P5 receptors (NPL 5). In the report, the action of reducing the heart rate as the adverse effect and the effect of reducing the number of circulating lymphocytes as the efficacy were observed at the same dose. Hence, it has been demonstrated that removing only the action on an S1P3 receptor cannot remove the cardiotoxicity in clinical practices, and that at least a portion of the cardiotoxic action observed from Fingolimod is a toxicity due to an agonist stimulus to an S1P1 receptor.

An S1P1 receptor is coupled to a suppressive Gα protein (hereinafter referred to as "Gαi"). In the heart, Gαi activated by an agonist stimulus to the receptor, together with Gβγ, activates the G protein-coupled inwardly-rectifying potassium channel (hereinafter referred to as "GIRK channel"). Since a complex of GIRK1 and GIRK4 is expressed in the heart, this agonist stimulus is believed to cause cardiotoxicity such as AV block and heart rate reduction (NPLs 5, 6).

It is reported that S1P, which is an endogenous agonist, against an S1P receptor generally exhibits a 50% activation concentration (EC50 value), as an agonist activity, of approximately around 10 nM although slightly varying depending on the evaluation method. On the other hand, the blood concentration of S1P in a normal healthy person is several hundreds of nM, indicating that S1P is present at a concentration several ten-fold higher than the EC50 value. However, no cardiotoxicity is induced in a normal healthy person. There is another contradiction: BAF312, which exhibits a similar EC50 value, has an effective blood concentration of several tens of nM as in the case of FTY-p, but the cardiotoxicity is expressed even at such a low concentration.

As described above, the mechanism of how an S1P receptor agonist exhibits an immunosuppressive activity as the main effect and cardiotoxicity as the adverse effect has not been elucidated sufficiently yet.

CITATION LIST

Patent Literature

[PTL 1] WO2013/094761

Non Patent Literatures

[NPL 1] Science, 296, 346-349 (2002)
[NPL 2] Journal of the American Society of Nephrology, 13 (4), 1073-1083 (2002)
[NPL 3] Journal of Biological Chemistry, 279 (14), 13839-13848 (2004)
[NPL 4] Molecular Pharmacology, 58, 449-454 (2000)
[NPL 5] British Journal of Pharmacology, 167, 1035-1047 (2012)
[NPL 6] Journal of Biological Chemistry, 276 (8), 5505-5510 (2001)
[NPL 7] Nature Chemical Biology, 8, 622-630 (2012)

SUMMARY OF INVENTION

Technical Problem

The present invention has been made in view of such circumstances as described above. An object of the present invention is to reveal a mechanism of how an S1P receptor agonist exhibits a main effect and an adverse effect, and to provide a method for evaluating a main effect and an adverse effect of an S1P receptor agonist on the basis of information on the mechanism. Another object of the present invention is to provide a screening method for an S1P receptor agonist having a strong main effect and a smaller adverse effect on the basis of the information on the mechanism.

Solution to Problem

There are a great number of molecules involved in the signal transduction of an S1P1 receptor. Even if only a Gα protein coupled to an S1P1 receptor is focused on among these molecules, there are also a great number of subtypes of the Gα protein. In such a circumstance, the present inventors have earnestly studied in order to achieve the above objects. As a result, the inventors have found that the immunosuppressive activity of an S1P1 receptor agonist correlates with the selective activity measured by cells expressing a combination of an S1P1 receptor with Gαi2 or Gαi3, and that the cardiotoxicity of an S1P1 receptor agonist correlates with the selective activity measured by cells expressing a combination of an S1P1 receptor with Gαi1. To be more specific, the present inventors have finally found out that Gαi1, Gαi2, and Gαi3 coupled to an S1P1 receptor are related to the immunosuppressive activity and the cardiotoxicity of an S1P receptor agonist.

Moreover, on the basis of such findings, the present inventors have found that detecting agonist activities specific to coupled Gα subunits (Gαi1, Gαi2, Gαi3) makes it possible to evaluate the strength of the immunosuppressive activity and the lowness of the cardiotoxicity of an S1P1 receptor agonist, and consequently to screen for an S1P1 receptor agonist having a potent immunosuppressive activity and a low cardiotoxicity. These discoveries have led to the completion of the present invention.

Thus, the present invention relates to an evaluation method and a screening method for an S1P1 receptor agonist, characterized by detecting a coupled Gα subunit-specific agonist activity against an S1P1 receptor. More specifically, the present invention provides the following.

(1) A method for evaluating a strength of an immunosuppressive activity of an S1P1 receptor agonist based on an agonist activity of the S1P1 receptor agonist against at least one of an S1P1 receptor coupled to Gαi2 and an S1P1 receptor coupled to Gαi3.

(2) A method for evaluating a strength of an immunosuppressive activity of an S1P1 receptor agonist, comprising the step of
measuring the S1P1 receptor agonist for agonist activities against an S1P1 receptor coupled to Gαi2 and an S1P1 receptor coupled to Gαi3, wherein
if the agonist activities against the S1P1 receptor coupled to Gαi2 and the S1P1 receptor coupled to Gαi3 are higher than an agonist activity against an S1P1 receptor coupled to Gαi1, the S1P1 receptor agonist is evaluated as being capable of exhibiting a potent immunosuppressive activity.

(3) A method for evaluating a strength of an immunosuppressive activity of an S1P1 receptor agonist, comprising the step of
measuring the S1P1 receptor agonist for agonist activities against an S1P1 receptor coupled to Gαi2 and an S1P1 receptor coupled to Gαi3, wherein
if the agonist activity against at least one of the S1P1 receptor coupled to Gαi2 and the S1P1 receptor coupled to Gαi3 is higher than that of an endogenous agonist S1P, the S1P1 receptor agonist is evaluated as being capable of exhibiting a potent immunosuppressive activity.

(4) A method for evaluating a probability of cardiotoxicity by an S1P1 receptor agonist based on an agonist activity of the S1P1 receptor agonist against an S1P1 receptor coupled to Gαi1.

(5) A method for evaluating a probability of cardiotoxicity by an S1P1 receptor agonist, comprising the step of
measuring the S1P1 receptor agonist for an agonist activity against an S1P1 receptor coupled to Gαi1, wherein if the agonist activity against the S1P1 receptor coupled to Gαi1 is lower than agonist activities against an S1P1 receptor coupled to Gαi2 and an S1P1 receptor coupled to Gαi3, the S1P1 receptor agonist is evaluated as being less likely to cause cardiotoxicity.

(6) A method for evaluating a probability of cardiotoxicity by an S1P1 receptor agonist, comprising the step of
measuring the S1P1 receptor agonist for an agonist activity against an S1P1 receptor coupled to Gαi1, wherein
if the agonist activity against the S1P1 receptor coupled to Gαi1 is lower than that of an endogenous agonist S1P, the S1P1 receptor agonist is evaluated as being less likely to cause cardiotoxicity.

(7) A screening method for an S1P1 receptor agonist, comprising the steps of:
(a) measuring a test compound for agonist activities against an S1P1 receptor coupled to Gαi1, an S1P1 receptor coupled to Gαi2, and an S1P1 receptor coupled to Gαi3, and
(b) selecting a compound having the agonist activities against the S1P1 receptor coupled to Gαi2 and the S1P1 receptor coupled to Gαi3 higher than the agonist activity against the S1P1 receptor coupled to Gαi1.

(8) The method according to (7), wherein a compound having the agonist activities against the S1P1 receptor coupled to Gαi2 and the S1P1 receptor coupled to Gαi3 30 times or more as high as the agonist activity against the S1P1 receptor coupled to Gαi1 is selected in step (b).

(9) A screening method for an S1P1 receptor agonist, comprising the steps of:
(a) measuring a test compound for agonist activities against an S1P1 receptor coupled to Gαi1, an S1P1 receptor coupled to Gαi2, and an S1P1 receptor coupled to Gαi3; and
(b) selecting a compound having the agonist activity against the S1P1 receptor coupled to Gαi1 lower than that of an endogenous agonist S1P and having the agonist activity against at least one of the S1P1 receptor coupled to Gαi2 and the S1P1 receptor coupled to Gαi3 higher than that of the endogenous agonist S1P.

Note that a representative amino acid sequence of the "S1P1 receptor" in the present invention and the base sequence of a corresponding mRNA thereof are respectively registered as NP001391.2 and NM001400.4 in the NCBI database.

Moreover, a representative amino acid sequence of "Gαi1 (whose gene name is GNAI1)" and the base sequence of a corresponding mRNA thereof are respectively registered as NP_002060.4 and NM002069.5 in the NCBI database.

Further, a representative amino acid sequence of "Gαi2 (whose gene name is GNAI2)" and the base sequence of a corresponding mRNA thereof are respectively registered as NP_002061.1 and NM002070.2 in the NCBI database.

Further, a representative amino acid sequence of "Gαi3 (whose gene name is GNAI3)" and the base sequence of a corresponding mRNA thereof are respectively registered as NP_006487.1 and NM006496.3 in the NCBI database.

Advantageous Effects of Invention

It has been impossible to separately evaluate a main effect (efficacy) and an adverse effect of an S1P1 receptor agonist by conventional methods for evaluating an agonist activity. The present invention makes it possible to separately evaluate a main effect and an adverse effect of an S1P1 receptor agonist by detecting agonist activities against an S1P1 receptor while distinguishing subtypes (Gαi1, Gαi2, Gαi3) of a Gα protein coupled to the S1P1 receptor. Moreover, this makes it possible to efficiently screen for an excellent S1P1 receptor agonist.

DESCRIPTION OF EMBODIMENTS

<Method for Evaluating Strength of Immunosuppressive Activity of S1P1 Receptor Agonist>

The present invention provides a method for evaluating a strength of an immunosuppressive activity of an S1P1 receptor agonist. In the present Examples, it has been found that the strength of the immunosuppressive activity of an S1P1 receptor agonist correlates with an agonist activity against an S1P1 receptor coupled to Gαi2 or an S1P1 receptor coupled to Gαi3. Thus, the evaluation method of the present invention is a method based on an agonist activity of an S1P1 receptor agonist against at least one of an S1P1 receptor coupled to Gαi2 and an S1P1 receptor coupled to Gαi3.

In the present invention, the "immunosuppressive activity" can be grasped, for example, on the basis of a reduction in the number of circulating lymphocytes. The number of circulating lymphocytes can be measured, for example, according to the method described in the present Example 2.

In the present invention, an agonist activity specific to a Gαi subtype can be measured, for example, according to the method described in the present Example 1 (2) (the method described in NPL 7). To be more specific, by allowing cells to express an S1P1 receptor and a particular Gα subtype together with Gγ2 and Gβ1, an agonist activity can be measured on the basis of a difference in percentage between the Gα protein and the Gβγ protein caused by an S1P1 receptor agonist.

Moreover, it is commonly known that when an S1P1 receptor is stimulated with an agonist, the intracellular cAMP level is regulated to a lower value. Thus, for example, using cells co-expressing an S1P1 receptor and a particular Gαi subtype, a Gαi subtype-specific agonist activity can also be measured on the basis of a reduction in the cAMP level by an S1P1 receptor agonist, under a condition where the intracellular cAMP level has been increased using forskolin or the like.

Further, deforming cells changes the resistance value formed in a monolayer membrane. A method is known which utilizes this phenomenon to measure a change in the resistance value caused by adding an S1P1 receptor agonist to a cultured monolayer of cells expressing an S1P receptor on a membrane (Invest Ophthalmol Vis Sci. 2005 June; 46 (6): 1927-33). Based on this method, a Gαi subtype-specific agonist activity can also be measured on the basis of a change in the resistance value caused by adding an S1P1 receptor agonist to cultured cells co-expressing an S1P1 receptor and a particular Gα subtype on a membrane, for example.

Furthermore, a method is commonly known in which a cell membrane expressing GPCR, a compound, and γ-[35S]GTP are allowed to react in a buffer, and then the amount of the labeled product binding to the membrane is quantified as the activity value of the agonist (Life Science Volume 74, Issue 4, 12 Dec. 2003, Pages 489-508). Thus, for example, using a cell membrane co-expressing an S1P1 receptor and a particular Gαi subtype, a Gαi subtype-specific agonist activity can also be measured on the basis of γ-[35S]GTP accumulation to the membrane fraction by GTP exchange reaction.

In one embodiment of the present invention, an S1P1 receptor agonist is measured for agonist activities against an S1P1 receptor coupled to Gαi2 and an S1P1 receptor coupled to Gαi3, and if the agonist activities against the S1P1 receptor coupled to Gαi2 and the S1P1 receptor coupled to Gαi3 are higher than an agonist activity against an S1P1 receptor coupled to Gαi1, the S1P1 receptor agonist is evaluated as being capable of exhibiting a potent immunosuppressive activity.

The agonist activities against the S1P1 receptor coupled to Gαi2 and the S1P1 receptor coupled to Gαi3 are preferably 10 times or more, more preferably 20 times or more, and furthermore preferably 30 times or more, as high as the agonist activity against the S1P1 receptor coupled to Gαi1.

Moreover, in another embodiment of the present invention, an S1P1 receptor agonist is measured for agonist activities against an S1P1 receptor coupled to Gαi2 and an S1P1 receptor coupled to Gαi3, and if the agonist activity against at least one of the S1P1 receptor coupled to Gαi2 and the S1P1 receptor coupled to Gαi3 is higher than that of an endogenous agonist S1P, the S1P1 receptor agonist is evaluated as being capable of exhibiting a potent immunosuppressive activity.

The agonist activity of the endogenous agonist S1P serving as a control may be measured when the agonist activities of an S1P1 receptor agonist are measured, or the value measured in advance may be used. For example, in the case where the measurement is performed according to the method described in the present Example 1 (2) (the method described in NPL 7), if the EC50 value (nM) of the agonist activity against an S1P1 receptor coupled to Gαi2 is 14 or less, or if the EC50 value (nM) of the agonist activity against an S1P1 receptor coupled to Gαi3 is 8 or less, the S1P1 receptor agonist is evaluated as being capable of exhibiting a potent immunosuppressive activity.

<Method for Evaluating Probability of Cardiotoxicity by S1P1 Receptor Agonist>

The present invention provides a method for evaluating a probability of cardiotoxicity by an S1P1 receptor agonist. In the present Examples, it has been found that the probability of cardiotoxicity by an S1P1 receptor agonist correlates with an agonist activity against an S1P1 receptor coupled to Gαi1. Thus, the evaluation method of the present invention is a method based on an agonist activity of an S1P1 receptor agonist against an S1P1 receptor coupled to Gαi1.

In the present invention, the "cardiotoxicity" can be grasped, for example, on the basis of AV block or heart rate reduction. The AV block can be measured, for example, according to the method described in the present Example 3. Meanwhile, the method for measuring a Gαi subtype-specific agonist activity in the present invention is as described above.

In one embodiment of the present invention, an S1P1 receptor agonist is measured for an agonist activity against an S1P1 receptor coupled to Gαi1, and if the agonist activity against the S1P1 receptor coupled to Gαi1 is lower than agonist activities against an S1P1 receptor coupled to Gαi2 and an S1P1 receptor coupled to Gαi3, the S1P1 receptor agonist is evaluated as being less likely to cause cardiotoxicity.

The agonist activity against the S1P1 receptor coupled to Gαi1 is preferably 1/10 or less, more preferably 1/20 or less, and furthermore preferably ⅓₀ or less, of the agonist activities against the S1P1 receptor coupled to Gαi2 and the S1P1 receptor coupled to Gαi3.

Moreover, in another embodiment of the present invention, an S1P1 receptor agonist is measured for an agonist activity against an S1P1 receptor coupled to Gαi1, and if the agonist activity against the S1P1 receptor coupled to Gαi1 is lower than that of an endogenous agonist S1P, the S1P1 receptor agonist is evaluated as being less likely to cause cardiotoxicity.

The agonist activity of the endogenous agonist S1P serving as a control may be measured when the agonist activity of an S1P1 receptor agonist is measured, or the value measured in advance may be used. For example, in the case where the measurement is performed according to the method described in the present Example 1 (2) (the method described in NPL 7), if the EC50 value (nM) of the agonist activity against an S1P1 receptor coupled to Gαi1 is more than 261, the S1P1 receptor agonist is evaluated as being less likely to cause cardiotoxicity.

<Screening Method for S1P1 Receptor Agonist>

The present invention provides a screening method for an S1P1 receptor agonist. In the present Examples, it has been revealed that the immunosuppressive activity of an S1P1 receptor agonist correlates with the selectivity for cells expressing a combination of an S1P1 receptor with Gαi2 or Gαi3 (the selective activity measured by cells expressing a combination of an S1P1 receptor with Gαi2 or Gαi3), and that the cardiotoxicity of an S1P1 receptor agonist correlates with the selectivity for cells expressing a combination of an S1P1 receptor with Gαi1 (the selective activity measured by cells expressing a combination of an S1P1 receptor with Gαi1). The screening method of the present invention utilizes such correlations.

The test compound used in the screening is not particularly limited. It is possible to use, for example, an synthetic low-molecular-weight compound library, an expression product from a gene library, a peptide library, an antibody, a substance released from a bacterium, a liquid extract or a culture supernatant of cells (microorganisms, plant cells, animal cells), a purified or partially purified polypeptide, an extract derived from a marine organism, plant, or animal, or a random phage peptide display library. Meanwhile, the method for detecting a Gαi subtype-specific agonist activity is as described above.

In one embodiment of the present invention, a test compound is measured for agonist activities against an S1P1 receptor coupled to Gαi1, an S1P1 receptor coupled to Gαi2, and an S1P1 receptor coupled to Gαi3, to select a compound having the agonist activities against the S1P1 receptor coupled to Gαi2 and the S1P1 receptor coupled to Gαi3 higher than the agonist activity against the S1P1 receptor coupled to Gαi1.

It is preferable to select a compound having the agonist activities against the S1P1 receptor coupled to Gαi2 and the S1P1 receptor coupled to Gαi3 10 times or more, more preferable to select a compound having the agonist activities 20 times or more, and furthermore preferable to select a compound having the agonist activities 30 times or more, as high as the agonist activity against the S1P1 receptor coupled to Gαi1.

Moreover, in another embodiment of the present invention, a test compound is measured for agonist activities against an S1P1 receptor coupled to Gαi1, an S1P1 receptor coupled to Gαi2, and an S1P1 receptor coupled to Gαi3, to select a compound having the agonist activity against the S1P1 receptor coupled to Gαi1 lower than that of an endogenous agonist S1P and having the agonist activity against at least one of the S1P1 receptor coupled to Gαi2 and the S1P1 receptor coupled to Gαi3 higher than that of the endogenous agonist S1P.

The agonist activities of the endogenous agonist SIP serving as a control may be measured when the agonist activities of the test compound are measured, or the values measured in advance may be used. For example, in the case where the measurement is performed according to the method described in the present Example 1 (2) (the method described in NPL 7), a compound is selected whose EC50 value (nM) of the agonist activity against an S1P1 receptor coupled to Gαi1 is more than 261, and whose EC50 value (nM) of the agonist activity against an S1P1 receptor coupled to Gαi2 is 14 or less or EC50 value (nM) of the agonist activity against an S1P1 receptor coupled to Gαi3 is 8 or less. The compound thus selected is considered to exhibit a potent immunosuppressive activity and have a low cardiotoxicity.

EXAMPLES

Hereinafter, the present invention will be described more specifically based on Examples. However, the present invention is not limited to the following Examples (Example 1) Evaluation of S1P1 Receptor Agonist for Immunosuppressive Activity (1) General Evaluation for S1P1 Receptor Agonist Activity As a general method for evaluating an S1P1 receptor agonist activity, there has been known a method which uses CHO cells expressing a S1P1 receptor, and the like to measure an agonist activity on the basis of binding to the receptor and a signal transduction activity through the binding (PTL 1). S1P, FTY-p, BAF312, a compound described in example 48 of European Patent No. 1826197 (hereinafter referred to as "compound A"), and a compound described in Example 2 of PTL 1 (hereinafter referred to as "compound B") were measured for S1P1 receptor agonist activities according to the method described in Experimental Example 1 of PTL 1. As a result, the S1P1 receptor agonist activities were respectively 6.4 nM, 0.08 nM, 3.0 nM, 0.3 nM, and 9.2 nM.

(2) Evaluation of Gα Protein Subtype-Specific S1P1 Receptor Agonist Activities

Next, the Gα protein subtype-specific S1P1 receptor agonist activities were evaluated according to the method described in NPL 7. Note that the expression conditions followed the section of "Supplementary Methods" in NPL 7, and the measurement conditions followed the section of "Bioluminescence resonance energy transfer measurement."

First, HEK 293T cells were allowed to co-express an S1P1 receptor, a particular Gα subtype (Gαi1, Gαi2, or Gαi3), Gγ2, and Gβ1. Then, on the basis of a difference in percentage between the Gα protein and the Gβγ protein caused by the endogenous agonist S1P, the agonist activity was measured. As a result, S1P had a 50% activation concentration (EC50 value) of 261 nM under the condition where Gαi1 was expressed, 14.6 nM under the condition where Gαi2 was expressed, and 8.4 nM under the condition where Gαi3 was expressed.

Next, under the same test conditions, FTY-p, BAF312, the compound A, and the compound B respectively had an EC50 value of 17.6 nM, 122 nM, 98 nM, and 640 nM under the condition where Gαi1 was expressed; respectively approximately 100 nM, 81 nM, 11 nM, and 6 nM under the condition where Gαi2 was expressed; and respectively 0.94 nM, 27 nM, 85 nM, and 19 nM under the condition where Gαi3 was expressed (Table 1).

TABLE 1

|  | S1P1-Gαi1 | S1P1-Gαi2 | S1P1-Gαi3 |
|---|---|---|---|
| S1P | 261 | 14.6 | 8.4 |
| FTY-p | 17.6 | 100 | 0.94 |
| BAF312 | 122 | 81 | 27 |
| Compound A | 98 | 11 | 85 |
| Compound B | 640 | 6 | 19 |

EC50 (nM)

This result revealed that FTY-p, BAF312, and the compound A had a strong activity against Gαi1 and a low selectivity for Gαi2 or Gαi3. On the other hand, it was revealed that the compound B had a weak activity against Gαi1 and high selectivities for Gαi2 and Gαi3. It can be concluded that the compound B is a highly biased agonist such that the bias in the activity observed in S1P is further increased.

(Example 2) Efficacy Evaluation of S1P1 Receptor Agonists

BAF312 or the compound B was orally administered to male SD rats at different doses. After 3, 6, and 24 hours, and the number of lymphocytic cells in blood was counted using a blood cell counter. As a result, in both cases, the number of lymphocytes was most significantly suppressing 6 hours after the administration, and the effects were observed by 24 hours.

The doses for suppressing the number of lymphocytic cells by 50% (ED50) after 6 hours and 24 hours were respectively 0.1 mg/kg and >1 mg/kg for BAF312, and 0.17 mg/kg and 0.65 mg/kg for the compound B. As a result of calculating the effective blood concentration after 24 hours, it was >208 nM for BAF312, and 176 nM for the compound B.

(Example 3) Cardiotoxicity Evaluation of S1P1 Receptor Agonist

The cardiotoxicity expression levels in guinea pigs under anesthesia as a cardiotoxicity evaluation model were examined using BAF312 and the compound B that exhibited an almost equivalent effective blood concentration thereto. In this model, the guinea pigs used were highly responsive to an S1P1 receptor, and further the model was capable of reliable detection of S1P1 receptor-dependent cardiotoxicity under anesthesia. An electrocardiograph and a pacing device were attached to the male guinea pigs whose breathings were artificially controlled under anesthesia, and the drugs were administered.

As a result, when 0.01 mg/kg of BAF312 was administered by infusion for 10 minutes, complete AV block was expressed in four out of four cases, and the complete AV block continued in all the cases until 1 hour elapsed.

On the other hand, when the compound B was administered under the same conditions, no expression of complete AV block was observed in any one out of four cases.

In addition, the blood concentrations of BAF312 and the compound B when the administrations were completed were respectively 17 nM and 91 nM. The blood concentrations after 1 hour were respectively <4 nM and 27 nM. This fact revealed that the compound B having a stronger biased activity was a compound with the weaker cardiotoxicity even though the blood concentration was the higher.

INDUSTRIAL APPLICABILITY

The present invention makes it possible to efficiently screen for an excellent S1P1 receptor agonist by separately evaluating a main effect (efficacy) and an adverse effect of the S1P1 receptor agonist. Therefore, the present invention can greatly contribute to the fields of pharmaceutical development and evaluation.

The invention claimed is:

1. A method for evaluating a strength of an immunosuppressive activity of an S1P1 a sphingosine-1-phosphate 1 (S1P1) receptor agonist, based on an agonist activity of the S1P1 receptor agonist against at least one of an S1P1 receptor coupled to Gαi2 and an S1P1 receptor coupled to Gαi3,
    said method comprising measuring the agonist activity of the S1P1 receptor agonist against at least one of an S1P1 receptor coupled to Gαi2, and an S1P1 receptor coupled to Gαi3,
    wherein if the agonist activities against the S1P1 receptor coupled to Gαi2 and/or the S1P1 receptor coupled to Gαi3 is higher than an agonist activity against an S1P1 receptor coupled to Gαi1, the S1P1 receptor agonist is evaluated as being capable of exhibiting a potent immunosuppressive activity.

2. A method for evaluating a strength of an immunosuppressive activity of an S1P1 receptor agonist, comprising the step of
    measuring the S1P1 receptor agonist for agonist activities against an S1P1 receptor coupled to Gαi2 and an S1P1 receptor coupled to Gαi3, wherein
    if the agonist activities against the S1P1 receptor coupled to Gαi2 and the S1P1 receptor coupled to Gαi3 are higher than an agonist activity against an S1P1 receptor coupled to Gαi1, the S1P1 receptor agonist is evaluated as being capable of exhibiting a potent immunosuppressive activity.

3. A method for evaluating a strength of an immunosuppressive activity of an S1P1 receptor agonist, comprising the step of
    measuring the S1P1 receptor agonist for agonist activities against an S1P1 receptor coupled to Gαi2 and an S1P1 receptor coupled to Gαi3, wherein
    if the agonist activity against at least one of the S1P1 receptor coupled to Gαi2 and the S1P1 receptor coupled to Gαi3 is higher than that of an endogenous agonist S1P, the S1P1 receptor agonist is evaluated as being capable of exhibiting a potent immunosuppressive activity.

4. A method for evaluating a probability of cardiotoxicity by an S1P1 receptor agonist, based on an agonist activity of the S1P1 receptor agonist against an S1P1 receptor coupled to Gαi1,
    said method comprising measuring the agonist activity of the S1P1 receptor agonist against an S1P1 receptor coupled to Gαi1,
    wherein if the agonist activity against the S1P1 receptor coupled to Gαi1 is lower than agonist activities against an S1P1 receptor coupled to Gαi2 and/or an S1P1 receptor coupled to Gαi3, the S1P1 receptor agonist is evaluated as being less likely to cause cardiotoxicity.

5. A method for evaluating a probability of cardiotoxicity by an S1P1 receptor agonist, comprising the step of measuring the S1P1 receptor agonist for an agonist activity against an S1P1 receptor coupled to Gαi1, wherein
if the agonist activity against the S1P1 receptor coupled to Gαi1 is lower than agonist activities against an S1P1 receptor coupled to Gαi2 and an S1P1 receptor coupled to Gαi3, the S1P1 receptor agonist is evaluated as being less likely to cause cardiotoxicity.

6. A method for evaluating a probability of cardiotoxicity by an S1P1 receptor agonist, comprising the step of
measuring the S1P1 receptor agonist for an agonist activity against an S1P1 receptor coupled to Gαi1, wherein
if the agonist activity against the S1P1 receptor coupled to Gαi1 is lower than that of an endogenous agonist S1P, the S1P1 receptor agonist is evaluated as being less likely to cause cardiotoxicity.

7. A screening method for an S1P1 receptor agonist, comprising the steps of:
(a) measuring a test compound for agonist activities against an S1P1 receptor coupled to Gαi1, an S1P1 receptor coupled to Gαi2, and an S1P1 receptor coupled to Gαi3; and
(b) selecting a compound having the agonist activities against the S1P1 receptor coupled to Gαi2 and the S1P1 receptor coupled to Gαi3 higher than the agonist activity against the S1P1 receptor coupled to Gαi1.

8. The method according to claim 7, wherein a compound having the agonist activities against the S1P1 receptor coupled to Gαi2 and the S1P1 receptor coupled to Gαi3 30 times or more as high as the agonist activity against the S1P1 receptor coupled to Gαi1 is selected in step (b).

9. A screening method for an S1P1 receptor agonist, comprising the steps of:
(a) measuring a test compound for agonist activities against an S1P1 receptor coupled to Gαi1, an S1P1 receptor coupled to Gαi2, and an S1P1 receptor coupled to Gαi3; and
(b) selecting a compound having the agonist activity against the S1P1 receptor coupled to Gαi1 lower than that of an endogenous agonist S1P and having the agonist activity against at least one of the S1P1 receptor coupled to Gαi2 and the S1P1 receptor coupled to Gαi3 higher than that of the endogenous agonist S1P.

10. A method for evaluating a strength of an immunosuppressive activity of an S1P1 receptor agonist, comprising:
measuring the S1P1 receptor agonist for agonist activities against an S1P1 receptor coupled to Gαi2 and/or an S1P1 receptor coupled to Gαi3,
wherein if the agonist activity against at least one of the S1P1 receptor coupled to Gαi2 and the S1P1 receptor coupled to Gαi3 is higher than that of an endogenous agonist, S1P, the S1P1 receptor agonist is evaluated as being capable of exhibiting a potent immunosuppressive activity.

* * * * *